United States Patent [19]

Iinuma

[11] Patent Number: 4,583,552
[45] Date of Patent: Apr. 22, 1986

[54] APPARATUS FOR OBSERVING BLOOD FLOW PATTERNS

[75] Inventor: Kazuhiro Iinuma, Tochigi, Japan

[73] Assignee: Tokyo Shibaura Denki Kabushiki Kaisha, Kawasaki, Japan

[21] Appl. No.: 642,651

[22] Filed: Aug. 21, 1984

[30] Foreign Application Priority Data

Aug. 25, 1983 [JP] Japan .................................. 58-156193

[51] Int. Cl.⁴ .............................................. A61B 10/00
[52] U.S. Cl. .................................... 128/663; 73/861.25
[58] Field of Search ....................... 128/663; 73/861.25

[56] References Cited

U.S. PATENT DOCUMENTS

| | | | |
|---|---|---|---|
| 4,103,679 | 8/1978 | Aronson | 128/663 |
| 4,205,687 | 6/1980 | White et al. | 128/663 |
| 4,318,413 | 3/1982 | Iinuma et al. | 128/663 X |
| 4,324,258 | 4/1982 | Huebscher et al. | 128/663 |
| 4,334,543 | 6/1982 | Fehr | 128/663 |

Primary Examiner—Kyle L. Howell
Assistant Examiner—Francis J. Jaworski
Attorney, Agent, or Firm—Finnegan, Henderson, Farabow, Garrett & Dunner

[57] ABSTRACT

An apparatus for observing blood flow patterns by utilizing ultrasonic beams which includes at least a pulse generator, a transducer, first and second phase detectors, and a monitor. The ultrasonic beams are transmitted and received by the transducer to obtain echo signals reflected from the body. The echo signals are phase-detected by the first phase detector to derive pulsed Doppler signals. The pulsed Doppler signals are phase-detected by the second phase detector to derive phase difference signals between the sampled pulsed Doppler signals. The sampling periods are determined in accordance with a depth of the body along a travel path of the ultrasonic beams. The blood flow patterns of the blood cells of the body are displayed on the monitor by processing the phase difference signals.

8 Claims, 16 Drawing Figures

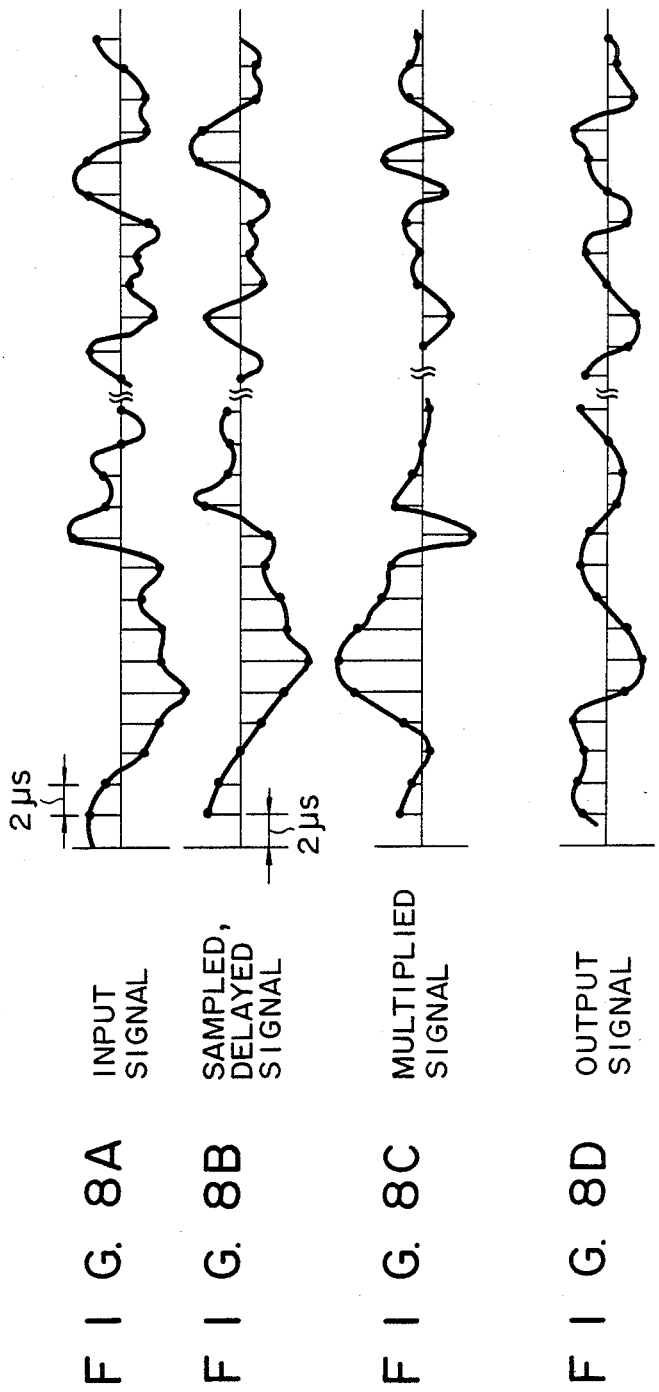

APPARATUS FOR OBSERVING BLOOD FLOW PATTERNS

BACKGROUND OF THE INVENTION

1. Field of the Invention

The present invention relates to an apparatus for observing blood flow patterns by way of ultrasonic beams, where the ultrasonic beams are transmitted to an object such as a biomedical body, and then ultrasonic echoes reflected from the object are processed by phase detectors, whereby the blood flow patterns, e.g., the blood flow patterns in a heart, can be visualized without giving invasive effects to the object.

2. Description of the Prior Art

Due to the development of a real-time ultrasonic tomographic apparatus, a tomographic image of a heart can now be observed. However, an intensity of ultrasonic echoes from a blood flow in the heart is lower than an intensity of ultrasonic echoes from a cardiac muscle by 40 dB or more. For this reason, the blood flow is normally displayed as an echo free component of the ultrasonic echoes in a cardiac tomograph. Therefore, the presence of a blood flow can be estimated, but the flow conditions, i.e., a flow direction, cannot be recognized.

It is known that invisible small bubbles (micro bubbles) are present in pysiological saline and strongly reflect ultrasonic beams. Utilizing this property of physiological saline, physiological saline is injected into a vein of an object to be examined and is circulated together with a blood flow in the heart, thereby displaying a blood flow in a tomographic image. This method is called "a contrast echo method" and is used in practice.

However, the contrast echo method involves an intravenous injection in the object (an invasive method). According to this method, only a blood flow image of the right atrium and ventricle (which pump out a blood flow to the lungs) is displayed. The blood flow of the left atrium and ventricle cannot be displayed although this flow must be clarified as a first priority for diagnostic purposes, resulting in inconvenience.

Another conventional method has been proposed where a blood flow is displayed two-dimensionally by utilizing a Doppler effect.

However, this method does not display the blood flow itself but displays the distribution map of blood flow, which does not give direct information about the direction of the blood flow. In other words, a flow speed is calculated and is displayed. Only the blood flow component (coming toward or going away from the emitting direction of the ultrasonic beam) parallel to the emission direction thereof is given. For this reason, even if the blood flow is oblique along the direction of the ultrasonic beam, information about an actual direction of the blood flow cannot be obtained.

The present invention has been made in consideration of those conventional inherent problems, and has as its object to provide an apparatus for observing blood flow patterns, wherein a blood current direction can be displayed by detecting blood flows parallel to an ultrasonic beam and perpendicular thereto in a noninvasive manner.

SUMMARY OF THE INVENTION

The object of the present invention may be accomplished by providing an apparatus for observing blood flow patterns by way of ultrasonic beams, comprising, a pulse generator for generating pulse signals as exciting pulse signals and also reference pulse signals, a transducer including a transducer element to which the exciting pulse signals are supplied so as to produce the ultrasonic beams therefrom, and from which echo signals are derived, the echo signals being produced by the ultrasonic beams which have been reflected from a body under investigation, a first phase detector for phase-detecting the echo signals based upon the reference pulse signals so as to obtain pulsed Doppler signals, a signal eliminator for eliminating signal components concerning clutter reflection of the body from the pulsed Doppler signals so as to derive pulsed Doppler shift signals, whereby the pulsed Doppler shift signals contain only signal components concerning blood cells of the blood flow in the body, a second phase detector for detecting phases of the sampled pulsed Doppler shift signals, and a display device for displaying the blood flow patterns of the blood cells from the detected phases of the sampled pulsed Doppler shift signals.

BRIEF DESCRIPTION OF THE DRAWINGS

The present invention is best understood by reference to the accompanying drawings, in which:

FIGS. 8A to 8D show waveforms of the major circuit elements shown in FIG. 7.

DETAILED DESCRIPTION OF THE PREFERRED EMBODIMENTS

The principle of the present invention will be described prior to a description of preferred embodiments thereof.

Ultrasonic echoes reflected by respective portions (organs and bones) of an object under examination are obtained such that a strong reflection signal from a muscle or the like is superposed on a weak reflection signal which has a signal strength of about 1/100 that of the strong reflection signal and which is reflected from blood cells or hemocytes. When the strong reflection signal (i.e., clutter reflection signal) from a clutter such as a muscle is eliminated from the ultrasonic echoes, the weak reflection signal from the blood cells or hemocytes can be obtained. Since the blood cells or hemocytes move together with a blood flow, the weak reflection signal is obtained as a Doppler shift signal corresponding to a blood flow speed. The phase of the Doppler shift signal varies in accordance with a distance from an emission point of the ultrasonic beam to a reflection point thereof. The phase is shifted at the same speed as the blood flow speed. Therefore, the blood flow speed can be detected in accordance with phase information.

Figure 1:
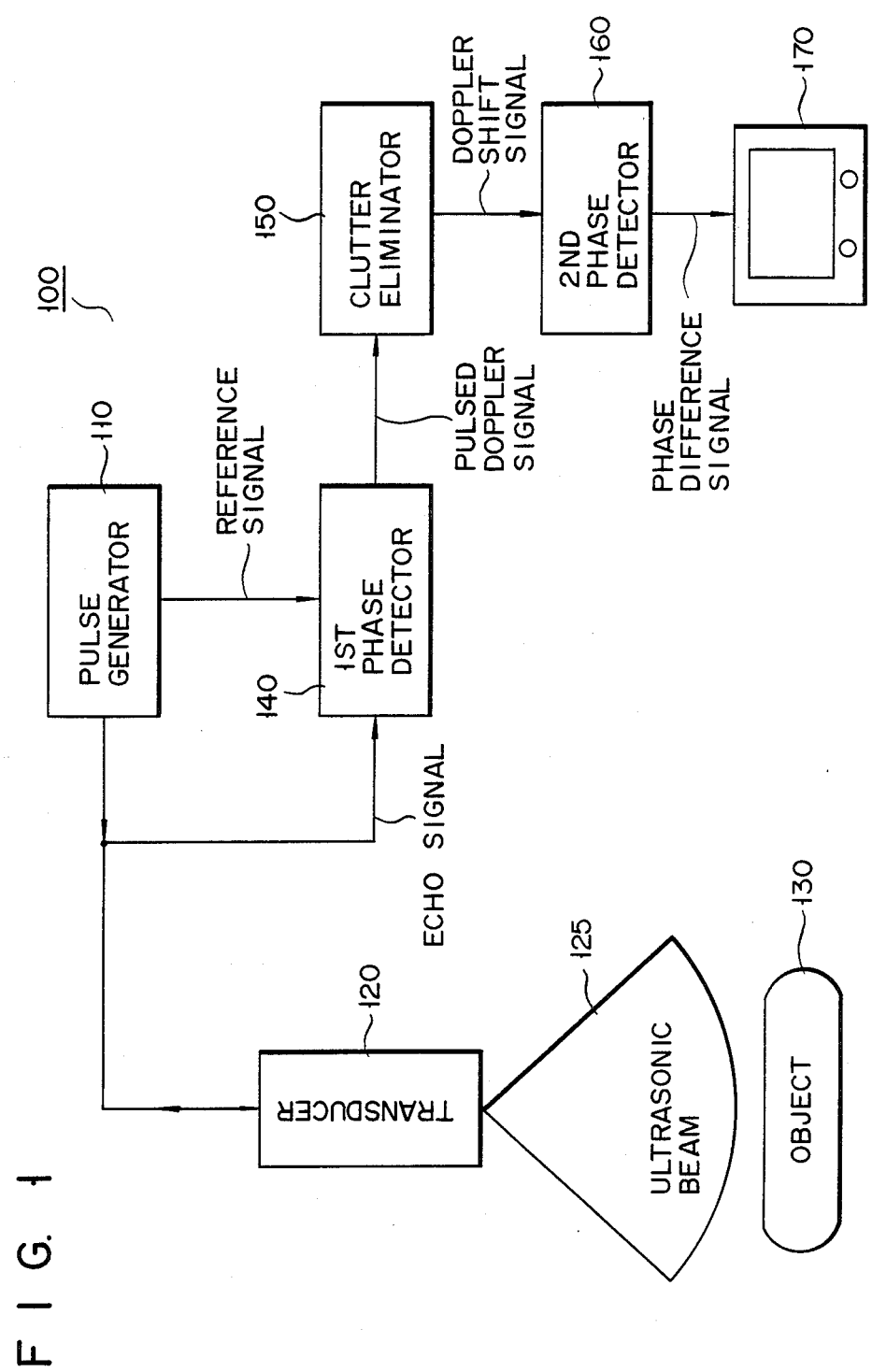
FIG. 1 is a system level block diagram illustrating the idea of a blood-flow-pattern observation apparatus according to the invention.

The principle idea of the present invention as described above will be described in detail with reference to the circuit diagram of FIG. 1.

By employing the pulsed Doppler method in an apparatus 100 of the present invention, a pulse generator 110 is arranged to generate exciting pulse signals so as to excite a transducer 120. At the same time, this exciting pulse signal serves as a reference signal of a first phase detector 140. The transducer 120 is excited in response to this exciting pulse signal and generates ultrasonic beams 125. An object 130, such as a patient is scanned with these ultrasonic beams 125 in, for example, a "sector" form. Reflected ultrasonic beams, i.e., ultrasonic echoes are obtained from the respective internal portions, e.g., blood cells of the object 130 and are received by the transducer 120. Thereafter, the ultrasonic echoes are converted to an echo pulse signal (to be referred to as an echo signal for brevity hereafter).

The echo signal is phase-detected by the first phase detector 140 in accordance with the reference signal (exciting pulse signal), thereby obtaining one-dimensional amplitude information, i.e., a pulsed Doppler signal.

A clutter signal component is eliminated by a clutter eliminator 150 from the pulsed Doppler signal of the first phase detector 140 to obtain a phase-detected echo signal component from blood cells. In other words, a Doppler shift signal is obtained.

This Doppler shift signal is phase-processed by a second phase detector 160. The echo signals are sequentially obtained from the respective internal portions of the object 130 at given time intervals. Echo signals from two given internal portions are sampled over time, and phase differences between every two echo signals of these two given portions sampled at identical moments are calculated to obtain a phase difference signal.

The phase difference signals are brightness-modulated, and the resultant phase difference signals are displayed on, for example, a TV monitor 170. As a result, the blood flow conditions such as the blood flow direction can be displayed.

It is alternatively possible to detect phases of the Doppler shift signals to directly display the blood flow patterns on the TV monitor 170.

Figure 2:
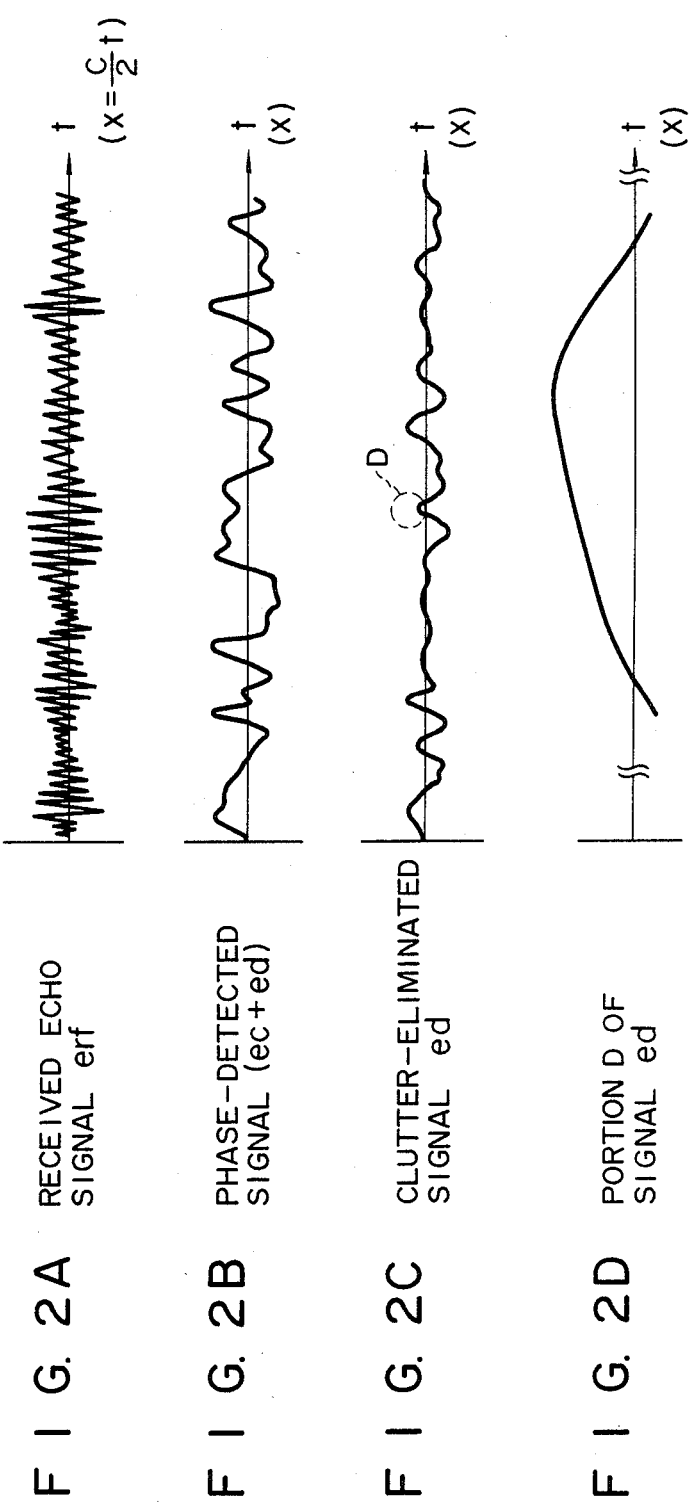
FIGS. 2A to 2D are waveform diagrams showing the waveforms for signals of the major circuit at several points within the FIG. 1 system.

More specifically, a received echo signal erf, obtained such that the echoes reflected from the object 130 are received by the transducer 120, is illustrated in FIG. 2A, and a time "t" between the reflection of the ultrasonic pulses and the reception thereof has a relationship with a distance "x" such that $x = ct/2$ (where $c$ = the velocity of sound in a medium). The abscissa (time) "t" in FIG. 2A corresponds to the distance "x". FIG. 2B shows a signal (a "phase-detected signal ec+ed") obtained by phase-detecting the received echo signal erf, as a superposed signal of a signal ec from the clutter and a weak signal ed from the blood flow. FIG. 2C shows the signal ed obtained by eliminating the clutter signal ec from the phase-detected signal (ec+ed). In practice, the amplitude of the clutter-eliminated signal ed is very small. However, this amplitude is illustrated in an amplified manner in FIG. 2C. FIG. 2D shows a signal component indicated by "D" in the signal ed of FIG. 2C which is enlarged with respect to the abscissa.

These signals are obtained for every rate pulse, i.e., for every time period $\Delta\tau$, where $\Delta\tau = 1/fr$ (fr being the rate frequency).

Figure 3:
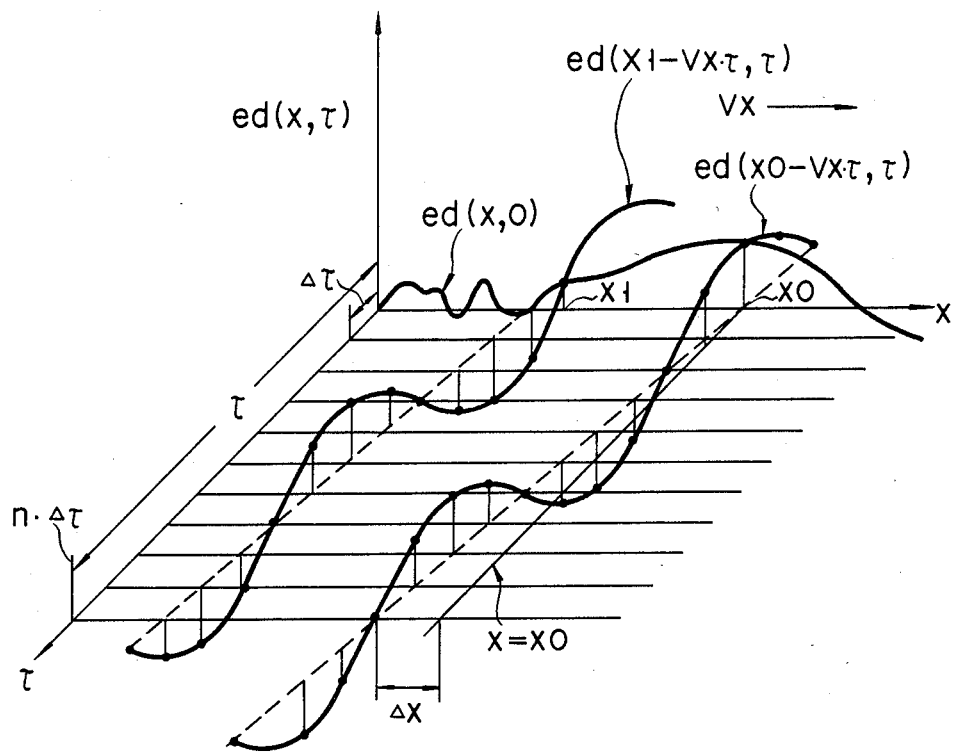
FIG. 3 is an illustration of waveforms of phase-detected signals relating to FIG. 2.

FIG. 3 shows values of the clutter-eliminated signal ed at the distance $x = x0$ for every rate. FIG. 3 is an illustrative representation of the principle of the present invention.

The center of a predetermined spatial sample volume $\Delta x$ (simply referred to as "sample volume") within the blood flow is plotted along the x-axis. The n reflection signals ed from the blood cells within the sample volume $\Delta x$ obtained from the first rate pulse to the nth rate pulse (after $\tau$ seconds, $\tau = n\Delta\tau$) are given as a function of the distance x and the time $\tau$ in equation (1) as follows:

$$ed(x,\tau) = A(x - Vx \cdot \tau) \cos\{2\pi \times fd(x)\tau + \theta(x - Vx \cdot \tau)\} \quad (1),$$

for $$ed(x,0) = A(x) \cos\{\theta(x)\} \quad (2),$$

$$\tau = n \cdot \Delta\tau = n/fr \quad (3),$$

where Vx is the x-axis component of the blood flow speed, and $A(x) \cos\{\theta(x)\}$ is the amplitude of the signal ed obtained by the first rate pulse ($\tau = 0$).

Since the blood cells move at the speed Vx along the x direction (the $-x$ direction in FIG. 3, i.e., a direction coming toward the transducer 120), the amplitude of the phase-detected signal changes. This change in amplitude is represented by a change $ed(x0 - Vx \cdot \tau, \tau)$ in a sinusoidal manner along the time axis $\tau$. This change in amplitude along the x direction is small. In a normal pulsed Doppler blood flow meter, when the clutter-eliminated signal ed at $x = x0$ is detected, a sinusoidal signal (along the $\tau$-axis) is detected as the Doppler signal. In equation (1), if $x = x0$ and $Vx \cdot \tau \approx 0$, $$ed(x0, \tau) = A(x0) \cos\{2\pi fd(x0)\tau + \theta(x0)\} \quad (4).$$

Therefore, the blood flow speed fd is detected. However, in practice $Vx \cdot \tau = 0$ is not established, but Vx is slightly deviated from 0, as shown in FIG. 3.

A phase of a reflection signal from a blood flow within a sample volume adjacent to the sample volume $\Delta x$ is different from that within the sample volume $\Delta x$. For example, this case indicates the clutter-eliminated signal ed at $x = x1$, as is given by $\theta(x)$ in equation (2). In this manner, the phases of the reflection signals vary in accordance with changes in positions x. However, when the sample volumes are adjacent to each other, the blood flow speeds, i.e., "fd" at these sample volumes, are substantially the same, and the coefficients A(x) for determining the amplitudes of the reflection signals are substantially the same as follows:

$$A(x + \Delta x) \approx A(x) \quad (5),$$

$$fd(x + \Delta x) \approx fd(x) \quad (6).$$

According to the present invention, in order to detect information of phase $\theta(x)$, a phase difference $\Delta\theta(x)$ between the reflection signals at the two adjacent sample volumes must be calculated.

When a product of ed(x,τ) and ed(x+Δx,τ) is given as E(x,τ), and equations (5) and (6) are used, the following relation is derived:

$$E(x,\tau) = (\tfrac{1}{2})A^2(x - Vx \cdot t) \times [\cos\{4\pi fd(x)\tau + \theta(x - Vx \cdot \tau) + \theta(x + \Delta x - Vx \cdot t)\} + \cos\{\theta(x - Vx \cdot \tau) - \theta(x + \Delta x - Vx \cdot \tau)\}] \quad (7).$$

When only the DC component is extracted and is given as $\bar{E}(x,\tau)$:

$$\bar{E}(x,\tau) = (\tfrac{1}{2})A^2(x - Vx \cdot \tau) \times \cos\{\Delta\theta(x - Vx \cdot \tau)\} \quad (8),$$

$$\Delta\theta(x) = \theta(x) - \theta(x + \Delta x) \quad (9).$$

The DC component $\bar{E}(x,\tau)$ moves at the speed Vx in the x direction. Therefore, a signal brightness-modulated with this DC component is displayed, and the blood flow direction can be displayed.

The principle of the present invention can be illustratively understood from FIG. 3. The waveform of the phase-detected signal (pulsed Doppler signal) from the first phase detector 140 of FIG. 1 is illustrted as the signal ed along the x-axis of FIG. 3 (a travel path of the ultrasonic beams). This phase-detected signal can be obtained for every one rate pulse. In practice, the n signals ed are obtained along the τ-axis (the time lapse). For illustrative convenience, only one wave, i.e., the pulsed doppler signal ed(x,0) is illustrated at τ=0. One rate pulse has a pulse width of Δτ, so that the signals ed are plotted parallel to each other along the τ-axis. These phase-detected signals ed could be obtained by a conventional Doppler method.

According to the present invention, the clutter signal components are eliminated from the pulsed Doppler signals, and pulsed Doppler shift signals at the respective points along the x-axis are sampled by range gating means. The phase differences between every two adjacent sampled Doppler shift signals are calculated by the second phase detector 160 that is the main feature of the invention. For illustrative convenience, only two sampled Doppler shift signals for calculating a phase difference therebetween have been selected, and their amplitude changes ed(x0 − Vx·T,τ) and ed(x1 − Vx·T,τ) are illustrated.

By calculating the phase difference between the clutter-eliminated Doppler shift signals ed, information of blood flow conditions such as a blood flow direction can be obtained in a real-time manner. The resultant information is displayed to observe the blood flow direction.

Furthermore, the present invention has been made on the basis of the following. According to the conventional pulsed Doppler method, the blood flow speed and a directional signal indicating that the blood flow is flowing toward or away from the transducer can be detected. However, the direction of the blood flow at each internal portion of the object cannot be displayed as well as flow conditions. However, according to the present invention, amplitude information at predetermined sampling points, e.g., x1 and x0, is obtained by the range gating means in accordance with the pulsed Doppler signals ed(x,0). The sampling periods are determined in accordance with a depth of the object along a travel path of the ultrasonic beams. The phase differences between every two adjacent sampled Doppler signals are obtained in accordance with these pieces of information. In this case, it is assumed that the phase relationship between the phase differences is maintained within a predetermined short time period. It should be noted that it is also possible to obtain the phase differences between two Doppler signals which have been arbitrarily sampled from the Doppler shift signal ed. The phase differences are acquired during the respective signal amplitudes of the corresponding sampling points. When the acquired phase differences are displayed, the blood flow direction is visible.

In addition, calculation and display of the phase differences can be performed in a real-time manner since an operation such as a Fourier transform need not be performed.

Figure 4:
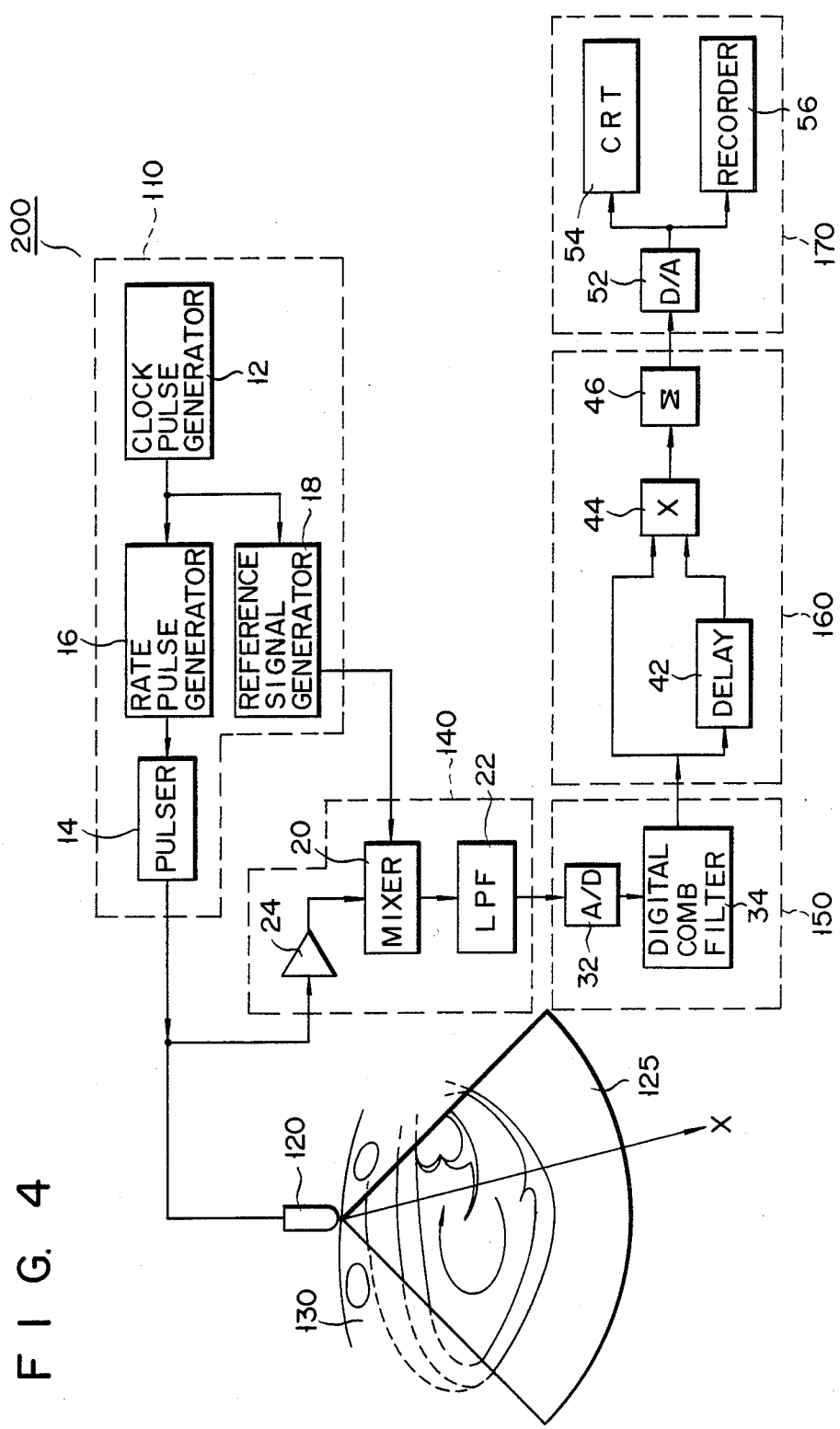
FIG. 4 shows a block diagram of an observation apparatus according to one preferred embodiment.

A circuit diagram of an apparatus 200 according to another embodiment employing the principle of the present invention is illustrated in FIG. 4 so as to describe this embodiment. The same circuit elements as in FIG. 1 denote the same parts in FIG. 4. Referring to FIG. 4, the pulse generator 110 comprises a clock pulse generator 12 for generating the reference clock pulse, a rate pulse generator 16 for frequency-dividing the reference clock pulse from the clock pulse generator 12 and generating a rate pulse, and a reference signal generator 18 for frequency-dividing the reference clock pulse and generating a reference signal to the first phase detector 140.

The first phase detector 140 for detecting a phase of an ultrasonic echo signal transduced by the transducer 120 has a mixer 20, a low-pass filter (LPF) 22 and an amplifier 24. In the first phase detector 140, the reflection signal from the amplifier 24 is multiplied with the reference signal having substantially the same center frequency as in the reflection signal and is generated from the reference signal generator 18, and a high-frequency component is cut off from the resultant product signal, thereby detecting the phase of the reflection signal. The clutter eliminator 150 for eliminating the clutter signal component from the output signal from the first phase detector 140 comprises an A/D converter 32 for converting to a digital signal the reflection signal generated from the low-pass filter 22, and a digital comb filter 34 for eliminating the cluttered signal ec from the reflection signal.

Figure 5A:
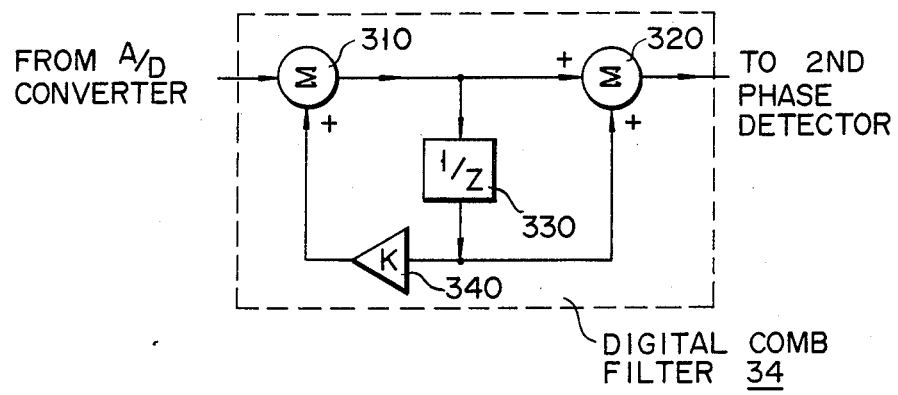
FIG. 5A is a block diagram of a digital comb filter in FIG. 4.
Figure 5B:
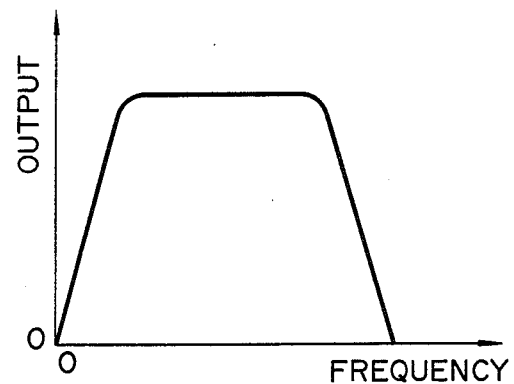
FIG. 5B is a characteristic curve of the filter shown in FIG. 5A.

The digital comb filter 34 may include adders 310 and 320, a shift register 330 and a multiplier 340, as shown in FIG. 5A. The shift register 330 delays the digital signal by a time period corresponding to one rate pulse. For example, if the rate pulse frequency fr is given to be 6 kHz, the rate pulse width of the digital comb filter, i.e., the delay time of the shift register 330, becomes 167 μs (1/6,000 ≈ 167 μs). The digital comb filter 34 has bandpass filter characteristics, as shown in FIG. 5B.

Figure 5C:
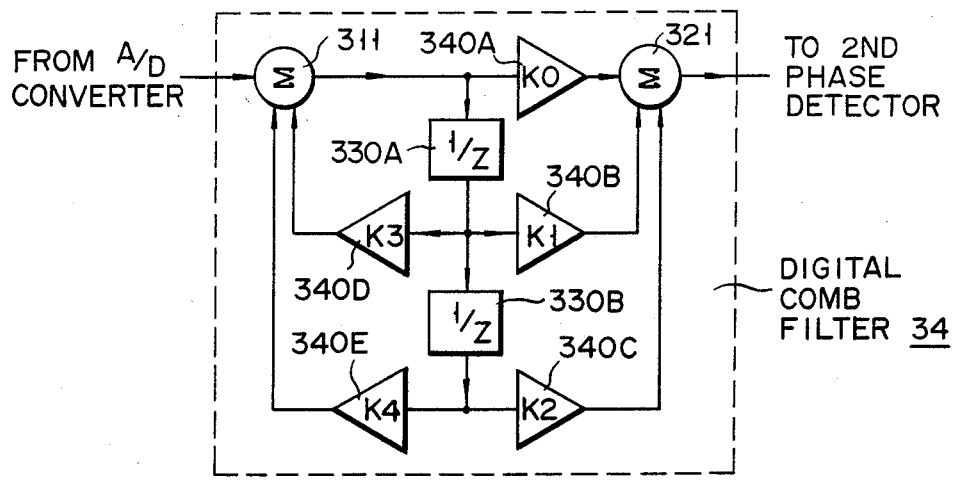
FIG. 5C is a block diagram of a modified digital comb filter.

If the digital comb filter 34 includes a higher-order filter having a plurality of stages, better filter characteristics can be obtained. For example, as shown in FIG. 5C, the digital comb filter 34 includes a single stage digital filter of the second order which consists of adders 311 and 321, shift registers 330A and 330B, and multipliers 340A, 340B, 340C, 340D and 340E. When the filtering operation is repeated by this digital comb filter 34, the desired filtering effect can be obtained. The output from the digital comb filter 34 is free from the cluttered signal ec and corresponds to the reflection signal ed whose waveform is illustrated in FIGS. 2C and 2D.

As shown in FIG. 4, the second phase detector 160 connected to the output of the clutter eliminator 150 has a delay circuit 42 for delaying the reflection signal ed from the blood cells by the delay time (approx. $2\Delta x/c$) corresponding to the pulse width, a multiplier 44 for multiplying the reflection signal ed from the blood cells with a delayed reflection signal edd from the delay circuit 42, and an adder 46 for simply adding the signals of several rates from the multiplier 44 n times. In this second phase detector 160, an AC component of the sum signal from the adder 46 is removed to generate a signal corresponding to $\overline{E}(x,\tau)$ in equation (8). In this manner, the clutter eliminator 150 and the second phase detector 160 connected to the output of the clutter eliminator 150 are designed in a digital circuit, so that the signal delay can be more accurate and simpler than that of an analogue circuit.

The display unit having the TV monitor 170 is arranged such that the signal corresponding to $\overline{E}(x,\tau)$ is converted by a D/A converter 52 to an analogue signal, and the resultant analogue signal is brightness-modulated by the TV monitor 170 and is displayed on a screen via a CRT 54 or stored in a recorder 56 in an M-mode.

The signals from the multiplier 44 are simply added n times by the adder 46 for every sampling rate $\Delta\tau(=1/fr)$, and the resultant product is represented by a single ultrasonic scanning line. In this case, a scanning line interval $\tau1$ is calculated as follows:

$$\tau1 = n\Delta\tau \tag{10}$$

A maximum value of the x-direction component (FIG. 4) of the detectable blood flow speed is:

$$Vxmax = Cfr/4f0 \tag{11}$$

a maximum distance $\Delta xmax$ of the blood flow is:

$$\Delta xmax = nC/4f0 \tag{12},$$

where C is the speed of sound in a medium, fr is the rate frequency, and f0 is the center frequency of the ultrasonic beam. The x direction corresponds to the x direction in FIG. 3. For example, if C=1,500 m/s, fr=6 kHz, f0=2.4 MHz and n=16, then:
Vxmax=94 cm/s,
$n\cdot\Delta\tau$=2.67 ms,
$\Delta xmax$=2.5 mm.

A two-dimensional blood flow observation using the apparatus 200 for observing blood flow patterns will be described in detail.

A slice of an internal portion, especially the heart of the object 130, is scanned with ultrasonic beams 125 emitted from the transducer 120. The beam scanning by the transducer 120 may be electronic scanning or mechanical scanning. For example, as shown in FIG. 6, when a sector angle $\widehat{H}$ is set at 20 degrees, and sector scanning is performed at every 0.5 degrees, the number of scanning lines becomes 40.

When a one-frame image of the TV monitor 54 includes 40 ultrasonic scanning lines, and a frame interval $\tau2$ is 6.67 ms, the following consideration will be made to determine whether or not observation for moving blood cells can be performed.

Figure 6:
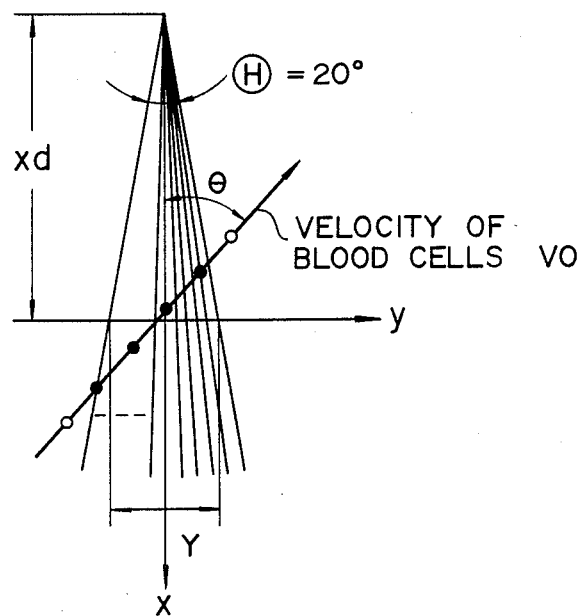
FIG. 6 is an illustration for explaining an ultrasonic beam scanning.

As shown in FIG. 6, when the blood cells located at the position xd are moving at an angle $\theta$ with respect to the ultrasonic beam direction x, velocity components Vx and Vy of the blood cells along the x direction of the ultrasonic beam and the y direction perpendicular thereto are given as follows:

$$Vx = U0 \cos\theta \tag{13},$$

$$Vy = U0 \sin\theta \tag{14},$$

where U0 is the absolute value of the velocity. On the other hand, the detectable velocities V0max, Vymax and Vxmax:

$$Vxmax = Cfr/4f0 \tag{15},$$

$$V0max = Cfr/4f0 \cos\theta \tag{16},$$

$$Vymax = Cfr \tan\theta/4f0 \tag{17}.$$

When the one-frame image includes N ultrasonic scanning lines, and maximum values of the x and y components and an absolute value of a distance of blood cells are $\Delta xmax$, $\Delta ymax$ and $\Delta lmax$, then:

$$\tau2 = N\cdot\Delta\tau = N/fr \tag{18},$$

$$\Delta xmax = NC/4f0 \tag{19},$$

$$\Delta ymax = NC \tan\theta/4f0 \tag{20},$$

$$\Delta lmax = NC/4f0 \cos\theta \tag{21}.$$

Substitution of N=40, fr=6 kHz, f0=2.4 MHz, $\theta$=45 degrees and $\tau2$=6.67 ms, as previously exemplified, into equations (18) to (21) yields:
$\Delta xmax = \Delta ymax = 6.25$ mm,
$\Delta lmax = 8.84$ mm.

On the other hand, a lateral view width at a position spaced by a distance xd from the transducer and the sector scanning angle are given to be Y and $\widehat{H}$, respectively, where:

$$Y = 2xd \tan\widehat{H}/2 \tag{22}.$$

For example, when xd=50 mm and $\widehat{H}$=20 degrees, Y=17.6 mm. A ratio of a moving distance $\Delta ymax$ of the blood cells having a detectable maximum velocity within one frame along the y direction to the view width Y is:

$$\Delta ymax/Y = (2fr\cdot xd\cdot\tan\widehat{H}/2)/N \cos\theta V0max \tag{23}$$

By using the values given above, $\Delta ymax/Y = 0.35$ is calculated.

The detectable blood cells having the highest speed are present within about three frames. The blood cells having a lower speed cross the screen in several tens of frames. Therefore, the blood flow can be observed by the initial values given above.

The operation after sector scanning will be described when the rate frequency is 6 kHz, the scanning line pitch is 0.5 degrees, the scanning angle is 20 degrees, the number of scanning lines is 40, and the frame interval is 6.67 ms (150 frames/second).

The ultrasonic beam is angularly shifted by 0.5 degrees for every rate. The reflection signal ed supplied to the amplifier 24 shown in FIG. 4 is a signal from the corresponding ultrasonic beam direction. When an aperture of the ultrasonic resonator is 12 mm and the ultrasonic beam frequency is 2.4 MHz, a −3 dB beam width at the ultrasonic receiver/transmitter is about 1.9 degrees, and a −6 dB beam width is about 3.6 degrees.

The reflection signals of about seven scanning lines are effectively processed by the digital comb filter 34 and the second phase detector 160. The processed signal having phase information coincides with the scanning direction of the ultrasonic beams 125 and is luminance-modulated on the TV monitor 54. The blood cell movement is thus displayed. In this case, the image on the TV monitor 54 has a sector shape since sector scanning is performed.

In this case, even if the blood cells move obliquely with respect to the beam direction, the velocity of these cells is represented by a component having the same direction as the beam direction. Therefore, the oblique flow direction can be displayed and observed per se. The blood flow component flowing in a direction perpendicular to the ultrasonic beam is eliminated by the clutter eliminator 150, and the eliminated signal is not supplied to the second phase detector 160 and cannot be detected. In this case, the orientation of the transducer 120 is changed to cause the ultrasonic beam to intersect obliquely with the blood flow so as to form an ultrasonic beam direction component, thereby visualizing the blood flow.

In addition, the reflection signal ed from the amplifier 24 shown in FIG. 4 is amplitude-detected by an amplitude detector (not shown) incorporated in the conventional ultrasonic CT apparatus, thereby reconstructing a cardiac tomographic image. As a result, the cardiac tomographic image and the blood flow image are superposed and simultaneously displayed on the TV monotor 54. Therefore, the effect of the apparatus for observing blood flow patterns according to the present invention can be further improved. If the monitor 54 includes a color TV monitor, a blood flow image can be displayed with light and dark red colors by utilizing an additional circuit, thereby obtaining a readily readable tomographic image.

In general, when a blood flow speed is increased, a view angle (scanning angle) must be decreased and the number of frames must be increased. On the other hand, the heart as a whole cannot be displayed at once when the scanning angle is as small as 20 degrees. In order to solve this problem, an electrocardiograph is added to the apparatus for observing blood flow patterns to acquire data for every heart beat, e.g., an R-wave in heart beat synchronization. The obtained data is temporarily stored in a memory (not shown) arranged in the TV monitor 170. The images at the adjacent scanning angle ranges are connected to each other to synthesize an image of a wider view. In this manner, the heart as a whole is effectively displayed. In this case, the average movement of the heart for each beat is displayed. This observation is sufficient for clinical purposes. Since the data is stored in the memory, it can be displayed repeatedly, in a slow motion manner, or in a still image display, thus providing other effects. For example, a 150-frame image at the view angle of 20 degrees can be clearly observed as a 30-frame image in a slow motion manner.

The present invention has been exemplified by a particular embodiment. However, the present invention is not limited to the particular embodiment described above. Various changes and modifications may be made within the scope and spirit of the invention.

Figure 7:
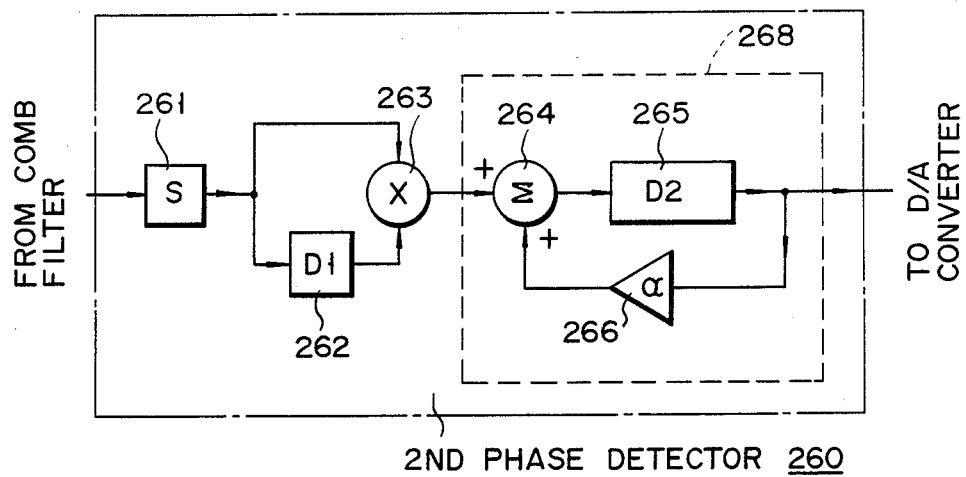
FIG. 7 shows a block diagram of a second phase detector according to another embodiment.

The second phase detector 160 in the above embodiment has the adder 46 for simply adding signals in units of n signals and generating a sum signal every time the n signals are added. However, as shown in FIG. 7, an adder 264 for generating a weighted sum for every rate can be used in place of the adder 46. Alternatively, a second phase detector 260 shown in FIG. 7 may be used in place of the second phase detector 160. This detector 260 comprises a series circuit which consists of a sampling circuit 261, a first delay circuit 262, a multiplier 263, and an adding circuit 268 having an adder 264, a second delay circuit 265 and a coefficient multiplier 266. The output from the digital comb filter 34, which is free from the cluttered signal, is supplied to the sampling circuit 261. In this case, as shown in FIG. 8A, data are sampled from the digital reflection signals ed for every pixel at the distance x (for every 2 $\mu$s when one pixel has a length of 1.5 mm), i.e., a length determined by a range gate width. The sampled data are supplied to the multiplier 263 and the first delay circuit 262 which are connected in parallel to each other. The first delay circuit 262 delays the input data by a time period of 2 $\mu$s corresponding to a one-pixel period shown in FIG. 8B. The delayed data is supplied to the multiplier 263. The multiplier 263 multiplies the input data and generates data whose waveform is shown in FIG. 8C. In this case, when a distance between the transducer 120 and the reflection point in the object 130 is given to be 10 cm, and the data of the reflecting point is included in the reflection signal, and a product for 67 pixels is generated from the multiplier 263 for every rate since the number of pixels is 67 (100/1.5). The product is supplied to the adder 264, and an output from the adder 264 is delayed by the second delay circuit 265 by one rate, i.e., $\Delta\tau$ (167 ns when the rate frequency is 6 kHz). The output from the second delay circuit 265 is multiplied by the coefficient multiplier 266 with a coefficient $\alpha$ ($\alpha<1$), and the resultant product is supplied to the adder 264. The signal obtained as the output from the second delay circuit 265 is substantially proportional to the cosine of the phase difference between the pixels of input signals (FIG. 8A), as shown in FIG. 8D. Therefore, $\overline{E}(x,\tau)$ is given as follows:

$$\overline{E}(x,\tau)=E(x,\tau)+\alpha \cdot E(x,\tau-\Delta\tau) \qquad (24).$$

As has been described in detail, according to the present invention, the blood flow conditions of internal portions, especially the heart of an object, can be displayed without using a contrast medium in a noninvasive manner and can be observed for clinical purposes. In addition, unlike the conventional Doppler method, a blood flow perpendicular to the ultrasonic beam can be observed. Therefore, the apparatus for observing blood flow patterns has the same effect as in heart angiography. In addition, when a color display is used, a cardiac muscle image can be clearly distinguished from a blood flow image, thereby allowing proper diagnostic procedures to be performed. A high speed blood flow can be observed in detail in a slow motion display.

In the above embodiment, the phase difference signals of the sampled Doppler shift signals were obtained so as to display the blood flow patterns. Alternatively, the blood flow patterns may be directly produced from the phases of the sampled Doppler shift signals.

What is claimed is:
1. An apparatus for imaging a blood flow of an object, comprising:
  ultrasonic transducer means for transmitting an ultrasonic interrogation pulse having a reference frequency in a beam toward said object and receiving echo signals reflected from said object and converting them into echo output signals;

scanning means for scanning said beam in the plane of said object;

first phase detecting means for producing a first plurality of phase detecting signals representative of phase differences between said echo output signals and said reference frequency;

second phase detecting means for dividing said first plurality of phase detecting signals into a plurality of sample signals representing sample volumes along said beam, and generating a second plurality of phase detecting signals representative of phase differences between sample signals for adjacent ones of said sample volumes; and displaying means for displaying said second plurality of phase detecting signals along said beam to provide an indication of blood flow in said object.

2. An apparatus according to claim 1, wherein said apparatus includes digital comb filter means for filtering said first phase detecting signals to eliminate clutter reflection of the object.

3. An apparatus as claimed in claim 2, wherein said digital comb filter means is constructed by first and second adders, a shift register, and a multiplier, whereby the shift register delays said first plurality of phase detecting signals for a delay time of approximately one rate pulse period.

4. An apparatus as claimed in claim 3, wherein a frequency of the rate pulse signals is selected to be 6 KHz, whereby the delay time is equal to approximately 167 $\mu$s.

5. An apparatus as claimed in claim 2, wherein said digital comb filter means is constructed by a second-order digital filter having first and second adders, first and second shift registers, and first, second, third, fourth and fifth multipliers.

6. An apparatus according to claim 1, wherein said scanning means steers said beam in a sector plane.

7. An apparatus according to claim 1, wherein said second phase detecting means includes a multiplier for multiplying said first plurality of phase detecting signals by the same delayed by one sample volume.

8. An apparatus as claimed in claim 7, wherein said second phase detecting means further includes an adder for adding the multiplied first plurality of phase detecting signals derived from said multiplier n times, n being a natural number except 1.

* * * * *

UNITED STATES PATENT AND TRADEMARK OFFICE
CERTIFICATE OF CORRECTION

PATENT NO. : 4,583,552
DATED : April 22, 1986
INVENTOR(S) : K. IINUMA

It is certified that error appears in the above-identified patent and that said Letters Patent is hereby corrected as shown below:

Title page, Assignee:

"Tokyo Shibaura Denki Kabushiki Kaisha" should correctly be --Kabushiki Kaisha Toshiba--.

Signed and Sealed this

Seventh Day of October, 1986

[SEAL]

Attest:

DONALD J. QUIGG

Attesting Officer

Commissioner of Patents and Trademarks